(12) United States Patent
Rigas

(10) Patent No.: US 9,678,058 B2
(45) Date of Patent: Jun. 13, 2017

(54) DIAGNOSTIC METHOD AND BREATH TESTING DEVICE

(76) Inventor: Anastasia Rigas, Setauket, NY (US)

( * ) Notice: Subject to any disclaimer, the term of this patent is extended or adjusted under 35 U.S.C. 154(b) by 12 days.

(21) Appl. No.: 13/420,321

(22) Filed: Mar. 14, 2012

(65) Prior Publication Data

US 2012/0234076 A1 Sep. 20, 2012

Related U.S. Application Data

(60) Provisional application No. 61/452,507, filed on Mar. 14, 2011.

(51) Int. Cl.
*G01N 33/497* (2006.01)
*G01N 33/84* (2006.01)
*A61B 5/08* (2006.01)
*A61B 5/00* (2006.01)
*A61B 5/097* (2006.01)

(52) U.S. Cl.
CPC ......... *G01N 33/497* (2013.01); *G01N 33/84* (2013.01); *A61B 5/082* (2013.01); *A61B 5/097* (2013.01); *A61B 5/4255* (2013.01); *G01N 2800/06* (2013.01)

(58) Field of Classification Search
CPC ......... A61B 5/097; A61B 5/082; A61B 5/083; A61B 5/091; A61B 5/08; G01N 33/45; G01N 33/497; G01N 33/4972; G01N 33/48; G01N 1/22; G01N 1/24; G01N 21/783; G01N 1/4044; G01N 1/405; G01N 33/004; G01N 33/0037; G01N 33/006; G01N 2800/065; G01N 2800/062; G01N 2800/067; G01N 33/84; G01N 2800/06

USPC ...... 73/23.3, 23.2, 31.05; 600/532, 300, 543
See application file for complete search history.

(56) References Cited

U.S. PATENT DOCUMENTS

| | | | |
|---|---|---|---|
| 3,852,036 A | 12/1974 | Burroughs | |
| 3,953,173 A | 4/1976 | Obayashi | |
| 4,007,063 A | 2/1977 | Yasuda | |
| 4,030,340 A | 6/1977 | Chang | |
| 4,140,106 A | 2/1979 | Kirmaier | |
| 4,169,369 A | 10/1979 | Chang | |
| 4,346,583 A * | 8/1982 | Hoogstraat | 73/23.3 |
| 4,430,191 A | 2/1984 | Sone | |

(Continued)

FOREIGN PATENT DOCUMENTS

DE  29902593 U1  8/1999
EP  2203563 A1  7/2010

(Continued)

OTHER PUBLICATIONS

Lupan, O., et al., Selective hydrogen gas nanosensor using individual ZnO nanowire with fast response at room temperature, Sensors and Actuators B: Chem, 2009, pp. 56-66, 144, Elsevier B.V.*

(Continued)

*Primary Examiner* — John Fitzgerald
*Assistant Examiner* — Marrit Eyassu
(74) *Attorney, Agent, or Firm* — Fredrikson & Byron, P.A.

(57) ABSTRACT

The present invention relates to a diagnostic method and breath-testing device for the diagnosis of Celiac Disease or other gastrointestinal malabsorption in adults and children, and uses a hydrogen selective sensor in the form of a ZnO nanowire-based sensor fabricated using a focused ion beam (FIB/SEM) instrument or a thin film.

9 Claims, 4 Drawing Sheets

(56) References Cited

U.S. PATENT DOCUMENTS

| | | | |
|---|---|---|---|
| 4,481,499 A | 11/1984 | Arima | |
| 4,753,916 A | 6/1988 | Carcia | |
| 4,823,803 A | 4/1989 | Nakamura | |
| 4,947,861 A | 8/1990 | Hamilton | |
| 5,037,525 A | 8/1991 | Badwal | |
| 5,055,441 A | 10/1991 | McCarron | |
| 5,069,220 A | 12/1991 | Casparie | |
| 5,252,292 A | 10/1993 | Hirata | |
| 5,531,225 A | 7/1996 | Nawata | |
| 5,546,004 A | 8/1996 | Schmelz | |
| 5,624,640 A | 4/1997 | Potthas | |
| 5,783,154 A | 7/1998 | Althainz | |
| 5,787,885 A | 8/1998 | Lemelson | |
| 5,811,662 A | 9/1998 | Williams | |
| 5,858,186 A | 1/1999 | Glass | |
| 5,969,231 A | 10/1999 | Qu | |
| 5,993,625 A | 11/1999 | Inoue | |
| 6,156,346 A | 12/2000 | Chen | |
| 6,173,602 B1 | 1/2001 | Mosely | |
| 6,173,603 B1 | 1/2001 | Horn | |
| 6,186,958 B1* | 2/2001 | Katzman et al. | 600/532 |
| 6,234,006 B1 | 5/2001 | Sunshine | |
| 6,319,724 B1 | 11/2001 | Lewis | |
| 6,411,905 B1 | 6/2002 | Guoliang | |
| 6,467,333 B2 | 10/2002 | Lewis | |
| 6,606,566 B1 | 8/2003 | Sunshine | |
| 6,609,068 B2 | 8/2003 | Cranley | |
| 6,620,109 B2 | 9/2003 | Hanson | |
| 6,660,231 B2 | 12/2003 | Moseley | |
| 6,703,241 B1 | 3/2004 | Sunshine | |
| 6,723,056 B1 | 4/2004 | Alving | |
| 6,767,732 B2 | 7/2004 | Alocilja | |
| 6,820,012 B2 | 11/2004 | Sunshine | |
| 6,839,636 B1 | 1/2005 | Sunshine | |
| 6,841,391 B2 | 1/2005 | Lewis | |
| 6,981,947 B2 | 1/2006 | Melker | |
| 7,014,612 B2 | 3/2006 | Hubbard | |
| 7,017,389 B2 | 3/2006 | Gouma | |
| 7,101,340 B1 | 9/2006 | Braun | |
| 7,104,963 B2* | 9/2006 | Melker et al. | 600/532 |
| 7,220,387 B2 | 5/2007 | Flaherty | |
| 7,338,454 B2* | 3/2008 | Butler et al. | 600/532 |
| 7,364,551 B2 | 4/2008 | Allen | |
| 7,522,040 B2 | 4/2009 | Passmore et al. | |
| 7,640,789 B2 | 1/2010 | Kim | |
| 7,687,275 B2 | 3/2010 | Burdinski | |
| 7,704,214 B2 | 4/2010 | Abraham-Fuchs | |
| 7,867,171 B2* | 1/2011 | Ben-Oren et al. | 600/532 |
| 7,950,271 B2 | 5/2011 | Novak | |
| 7,981,215 B2 | 7/2011 | Gouma | |
| 8,263,002 B1* | 9/2012 | Chow et al. | 422/83 |
| 8,343,484 B2 | 1/2013 | Farmer | |
| 8,485,983 B2 | 7/2013 | Gouma | |
| 9,289,155 B2 | 3/2016 | Rigas | |
| 2002/0011569 A1 | 1/2002 | Mori | |
| 2003/0008407 A1 | 1/2003 | Fu | |
| 2003/0105407 A1* | 6/2003 | Pearce et al. | 600/532 |
| 2003/0175699 A1 | 9/2003 | Tachikawa | |
| 2003/0208133 A1 | 11/2003 | Mault | |
| 2003/0217586 A1 | 11/2003 | Gouma | |
| 2004/0077965 A1 | 4/2004 | Hubbard | |
| 2005/0100535 A1* | 5/2005 | Farmer | A61K 35/742 424/93.46 |
| 2005/0129573 A1 | 6/2005 | Gabriel | |
| 2005/0171449 A1 | 8/2005 | Suslick | |
| 2006/0074335 A1* | 4/2006 | Ben-Oren et al. | 600/532 |
| 2006/0147496 A1* | 7/2006 | Lin | A61K 38/54 424/439 |
| 2006/0174385 A1 | 8/2006 | Gruber | |
| 2006/0277974 A1 | 12/2006 | Gouma | |
| 2007/0048181 A1 | 3/2007 | Chang | |
| 2007/0167691 A1 | 7/2007 | Causevic | |
| 2007/0256477 A1 | 11/2007 | Moor | |
| 2007/0272901 A1 | 11/2007 | Gouma | |
| 2008/0077037 A1* | 3/2008 | Gouma et al. | 600/532 |
| 2008/0093226 A1 | 4/2008 | Briman | |
| 2009/0294303 A1 | 12/2009 | Fischer | |
| 2010/0012919 A1* | 1/2010 | Park et al. | 257/9 |
| 2010/0089772 A1* | 4/2010 | Deshusses et al. | 205/781 |
| 2010/0209507 A1* | 8/2010 | Lin et al. | 424/474 |
| 2010/0212403 A1* | 8/2010 | Seal et al. | 73/31.06 |
| 2011/0056846 A1 | 3/2011 | Neethirajan | |
| 2011/0061446 A1 | 3/2011 | Gouma | |
| 2012/0034646 A1 | 2/2012 | Rigas | |
| 2012/0065534 A1 | 3/2012 | Rigas | |
| 2012/0186999 A1 | 7/2012 | Walton | |
| 2012/0234076 A1 | 9/2012 | Rigas | |
| 2012/0237968 A1 | 9/2012 | Rigas | |
| 2014/0221863 A1 | 8/2014 | Rigas | |
| 2014/0330153 A1 | 11/2014 | Gouma | |
| 2015/0250407 A1 | 9/2015 | Rigas | |

FOREIGN PATENT DOCUMENTS

| | | |
|---|---|---|
| EP | 2685891 A2 | 1/2014 |
| WO | 0206822 A1 | 1/2002 |
| WO | 03041565 A2 | 5/2003 |
| WO | 2009039152 A1 | 3/2009 |
| WO | 2011004567 A1 | 1/2011 |
| WO | 2012125734 A2 | 9/2012 |
| WO | 2012125745 A2 | 9/2012 |
| WO | 2014056961 A1 | 4/2014 |
| WO | 2014063169 A1 | 4/2014 |
| WO | 2015179751 A1 | 11/2015 |
| WO | 2015179755 A1 | 11/2015 |

OTHER PUBLICATIONS

Rana, S.V., et al., Influece of previously ingested wheat on fasting breath hydrogen in celiac patients, Dig Dis Sci, Jun. 2009, pp. 1276-1279, 54(6), Springer Science+Business Media, LLC.*

Francesc Casellas, Md, et al., Hydrogen Breath Test with D-Xylose for Celiac Disease Screening is as Useful in the Elderly as in Other Age Groups, Oct. 2001, Digestive Diseases and Sciences, vol. 46, No. 10, pp. 2201-2205.*

Corazza GR, et al., Fasting breath hydrogen in celiac disease, Pub Med, Gastroenterology. Jul. 1987;93(1):53-8.*

Tveito, K, et al., 13C-xylose and 14C-xylose breath tests for the diagnosis of coeliac disease, Scandinavian J Gastroenterology, 2008, pp. 166-173, 43(2), SUNY State University of New York, Stony Brook.

Tveito, K, et al., A novel one-hour 13C-sorbitol breath test versus the H2-sorbitol breath test for assessment of coeliac disease, Scandinavian J Gastroenterology, 2009, pp. 813-819, 44, Suny State University of New York, Stony Brook.

Hryniuk, Alexa, et al., A preliminary investigation of exhaled breath from patients with celiac disease using selected ion flow tube mass spectrometry, J Gastrointestin Liver Dis., Mar. 2010, pp. 15-20, 19(1), Lakehead University, Thunder Bay, Ontario, Canada.

Rana, S.V., et al., Influence of previously ingested wheat on fasting breath hydrogen in celiac patients, Dig Dis Sci, Jun. 2009, pp. 1276-1279, 54(6), Springer Science+Business Media, LLC.

Supplementary European Search Report of European Pat. App. No. 12757976.1, Feb. 18, 2015, 9 pages, European Patent Office, Munich, Germany.

International Preliminary Report on Patentability of International Pat. App. No. PCT/US2012/029087, Feb. 4, 2014, 5 pages, The International Bureau of WIPO, Geneva, Switzerland.

International Search Report and Written Opinion of the International Searching Authority, International Pat. App. No. PCT/US2012/029087, Jul. 6, 2012, 6 pages, International Searching Authority, Alexandria, Virginia.

Abdel-Saheb, Ibrahim, Memorandum: Review of Urea, as an Active and Inert Ingredient Environmental Protection Agency, (2001) Retrieved from Internet on Apr. 1, 2016 at <URL: http://web.archive.org/web/20040722194412/http://www.epa.gov/oppsrrd1/reregistration/urea/UreaEnviron.pdf> 14 pages.

Agha, Aamer et al., Evidence-based examination of the African enigma in relation to Helicobacter pylori infection. Scandinavian Journal of Gastroenterology (2005) 40:523-529, Taylor & Francis Group Ltd, United Kingdom.

(56) References Cited

OTHER PUBLICATIONS

ALCOSCAN™ Al2000 Alcohol Breath Analyzer, Craig Medical Distribution Inc., 3 pages, retrieved from Internet on Mar. 29, 3026 at <URL: http://www.craigmedical.com/alcoscan_AL_2000.htm.
Biesiekierski, Jessica R. et al., No Effects of Gluten in Patients With Self-Reported Non-Celiac Gluten Sensitivity After Dietary Reduction of Fermentable, Poorly Absorbed, Short-Chain Carbohydrates. Gastroenterology (2013) vol. 145, 12 pages.
Brandli, O. et al., Lung function in healthy never smoking adults: reference values and lower limits of normal of a Swiss population. Thorax (1996) 51:277-283. Retrieved from the Internet on Mar. 19, 2016 at < http://thorax.bmj.com/>.
Brown, L. M. Helicobacter pylori: epidemiology and routes of transmission. Epidemiol Rev (2000) 22:283-297.
Chen, Jyh-Cherng et al., Removal of carbon dioxide by a spray dryer, Chemosphere, (2005) 59:99-105, <doi:10.1016/j.chemosphere.2004.09.076>.
Chung, Yong-Keun et al., Gas sensing properties of WO3 thick film for NO2 gas dependent on process condition, Sensors and Actuators B: Chemical (1999) 60:49-56 <doi:10.1016/S0925-4005(99)00243-9>.
Cutler, Alan F. et al., Accuracy of invasive and noninvasive tests to diagnose Helicobacter pylori infection, Gastroenterology (1995) 109:136-141, American Gastroenterological Association.
Cutler, Alan F., Testing for Helicobacter pylori in clinical practice. Symposium on Helicobacter Pylori, Am J Med (1996) 100:35S-41S, Supplement 5 [Discussion pp. 39S-41S].
Dai, Liming et al., Sensors and sensor arrays based on conjugated polymers and carbon nanotubes; Pure App. Chem., vol. 74, No. 9, pp. 1753-1772, 2002.
Decarbite®, P.W. Perkins Co., Inc., Safety Data Sheet (Jan. 5, 2015) 4 pages.
Delaney, B. et al., Review article: Helicobacter pylori and gastroesophageal reflux disease. Aliment Pharmscol Ther (2005) 22 Suppl 1 :32-40.
Di Francesco, F., et al., Breath analysis: trends in techniques and clinical applications. Microchemical Journal (2005) 79:105-410.
Dunn, B. E et al., Helicobacter pylori. Clinical Microbiology Reviews (1997) pp. 720-741, vol. 10, Issue 4, retrieved from the Internet on Mar. 19, 2016 at <URL: http://cmr.asm.org/>.
Dutta, Prabir, et al., Interaction of Carbon Monoxide with Anatase Surfaces at High Temperatures: Optimization of a Carbon Monoxide Sensor, J. Phys. Chem. B., 103, pp. 4412-4419, (1999).
Dutta, Ritaban et al., Classification of Ear, Nose and Throat Bacteria Using a Neural-Network-Based Electronic Nose; Mrs Bulletin, Oct. 2004, pp. 709-713, Materials Research Society http://www.mrs.org/publications/.
Eshun, J. K. et al., Comparison of immunohistochemistry and silver stain for the diagnosis of pediatric Helicobacter pylori infection in urease-negative gastric biopsies. Pediatr Dev Patho (2001) 4:82-88.
Eslick, G. D. et al., Association of Helicobacter pylori infection with gastric carcinoma: a meta-analysis. Am J Gastroenterol (1999) 94:(9) 2373-2379.
Extended European Search Report for European Pat. App. No. 08832402, titled, Detection of H. Pylori Utilizing Unlabeled Urea, European Patent Office, Jun. 13, 2013, 9 pages, Munich, Germany.
Extended European Search Report for European Pat. App. No. 127579761 titled, Diagnostic Method and Breath Testing Device, European Patent Office, Feb. 18, 2015, 9 pages, Munich, Germany.
Ferroni, A. et al., Nanosized thin films of tungsten-titanium mixed oxides as gas sensors, Sensors and Actuators B 58 (1999) pp. 289-294.
Gatta, L. et al., A rapid, low-dose, 13C-urea tablet for the detection of Helicobacter pylori infection before and after treatment. Aliment Pharmacal Ther (2003) 17:793-798.
Giner Electrochemical (Trace) Gas Sensors. Datasheet [online]. Giner, Inc., retrieved from the Internet on Apr. 22, 2016 at <URL: http://www.ginerinc.com/products.php?a=TGSI>.
Gisbert, J. P. et al., Accuracy of Helicobacter pylori Diagnostic Tests in Patients with Bleeding Peptic Ulcer: A Systematic Review and Meta-analysis. Am J Gastroenterol (2006) 101:848-863.
Gisbert, J. P. et al., Review article: 13C-urea breath test in the diagnosis of Helicobacter pylori infection—a critical review. Aliment Pharmacal Ther (2004) 20:1001-1017.
Gisbert, J. P., The recurrence of Helicobacter pylori infection: incidence and variables influencing it. A critical review. Am J Gastroenterol (2005) 100:2083-2099.
Go, M. F. Review article: natural history and epidemiology of Helicobacter pylori infection. Aliment Pharmacol Ther 16 Suppl (2002) 1:3-15.
Gouma, P. et al., Novel Materials and Applications of Electronic Noses and Tongues; MRS. Bulletin Oct. 2004, pp. 697-702.
Gouma, P. I. et al., Microstructural Characterization of Sensors based on Electronic Ceramic Materials, JOM, 50 (11), presented as JOM-e., Nov. 1998, 15 pages.
Gouma, P. I. et al., Selective nanoprobes for 'signalling gases', Nanotechnology 17 (2006) S48-S53, retrieved from the Internet on Mar. 19, 2016 at <URL: http://iopscience.iop.org/article/10.1088/0957-4484/17/4/008/meta; sessionid=DEE5CDBA0DD81DDF45C9D0CA79F53344.c3>.
Gouma, P. I. et al., Structural Stability of Titania Thin Films, Nanostructured Materials (1999) 11(8), pp. 1231-1237.
Gouma, P. I. et al., TiO2-based Gas Sensors as Thick or Thin Films: An Evaluation of the Microstructure. Proceedings of the International Symposium on Dielectric Ceramics, May 2-6, 1998 and Ceramic Transactions: Dielectric Ceramic Materials, (1999) vol. 100, pp. 419-428, The American Ceramic Society, Westerville, Ohio.
Gouma, Pelagia I. et al., Fabrication of Free-Standing Titania-Based Gas Sensors by the Oxidation of Metallic Titanium Foils. J. Am Ceramic. Soc., 83(4), pp. 1007-1009, 2000.
Graham, D. Y., et al., Challenge model for Helicobacter pylori infection in human volunteers. Gut (2004) 53:1235-1243, retrieved the Internet on Mar. 19, 2016 at <URL: http://gut.bmj.com/>. Published by group.bmj.com.
Guidi, V. et al., Nanosized Ti-doped MoO3 thin films for gas-sensing application. Sens and Act B, (2001) 77:555-560.
Harris, Adam et al., Treating Helicobacter pylori-the best is yet to come? Gut (1996) 39:781-783, retrieved from the internet on Mar. 19, 2016 at <URL: http://gut.bmj.com/>. Published by group.bmj.com.
He, Lifang et al., Gas Sensors for ammonia detection based on polyaniline-coated multi-wall carbon nanotubes (2009) Materials Science and Engineering B, 163:76-81.
Helmus, Michael N. et al., Nanotechnology-enabled chemical sensors and biosensors. American Laboratory (2006) 38:34-38.
Hu, Li Tai et al., Purification and N-terminal analysis of urease from Helicobacter pylori. Infect Immun (1990) 58:992-998.
Humerfelt, S. et al., Forced expiratory volume in 1 second (FEV1) and forced vital capacity (FVC) variability in asymptomatic neversmoking men. Clin Physio. (1998) 18:387-396.
Hunt, R. H., Peptic Ulcer Disease: Defining the Treatment Strategies in the Era of Helicobacter pylori. Am J Gastroentero. (1997) 92:36S-40S; discussion 40S-43S.
Imawan, C. et al., A new preparation method for sputtered MoO3 multilayers for the application in gas layers, Sensors and Actuators B. 78 (2001) pp. 119-125.
Imawan, C. et al., Gas-sensing characteristics of modified-MoO2 thin films using Ti-overlayers for NH3 gas sensors, Sensors and Actuators B 64 (2000) pp. 193-197.
International Search Report and Written Opinion for Intl. Pat. App. No. PCT/US2015/032162 titled, Breath Analyzer and Breath Test Method, International Searching Authority, Oct. 16, 2015, 16 pages, U.S. Patent and Trademark Office, Alexandria, Virginia.
International Search Report for Intl. Pat App. No. PCT/US2012/029103 titled, Detector and Method for Detection of H. Pylori, International Searching Authority, Jun. 13, 2012, 3 pages, U.S. Patent and Trademark Office, Alexandria, Virginia.

(56) References Cited

OTHER PUBLICATIONS

Kato, Seiichi et al., Diagnostic Accuracy of the 13C-Urea Breath Test for Childhood Helicobacter pylori Infection: A Multicenter Japanese Study The American J of Gastroenterology, (2002) 97(7):1668-1673.
Kearney, David J. et al., Breath Ammonia Measurement in Helicobacter pylori Infection, Dig Dis Sci (2002) 17:2523-2530.
Kharitonov, Sergei A. et al., Exhaled markers of pulmonary disease. Am J Respir Crit Care Med (2001) 163:1693-1722.
Klein, Peter O. et al., Noninvasive detection of Helicobacter pylori infection in clinical practice: the 13C urea breath test. Am J Gastroentero. (1996) 91 :690-694.
Leong, R.W. et al., Review article: Helicobacter species and hepatobiliary diseases. Aliment Pharmacal Ther (2002) 16:1037-1045.
Leung, Wai K. Helicobacter pylori and Gastric Neoplasia. Contrib Microbio (2006) 13:66-80.
Livage, Jacques et al., Encapsulation of biomolecules in silica gels. J. Phys.: Condens. Matter 13 (2001) pp. R673-R691, retrieved from the Internet on Mar. 20, 2016 at <URL: http://iopscience.iop.org/article/10.1088/0953-8984/13/33/202/pdf>.
Marquis, Brent T. et al., A semiconducting metal oxide sensor array for the detection of NOx and NH3, Sensors and Actuators B 77 (2001) pp. 100-110.
Minoli, Giorgio et al., A Simplified Urea Breath Test for the Diagnosis of Helicobacter pylori Infection Using the LARA System. Laser Assisted Ratio Analyzer. J Clin Gastroenterol. (1998) 26:264-266; retrieved from the Internet on Mar. 28, 2016 at <URL: http://journals.lww.com/jcge/Abstract/1998/06000/A_Simplified_Urea_Breath_Test_for_the_Diagnosis_of.9.aspx>.
Monteiro, Lurdes et al., Evaluation of performances of three DNA enzyme immunoassays for detection of Helicobacter pylori PCR products from biopsy specimens. J Clin Microbiol. (1997) 35:2931-2936.
Murakami, Kazunari et al., Latest insights into the effects of Helicobacter pylori infection on gastric carcinogenesis. World J Gastroentero. (2006) 12:2713-2720.
Murnick, D. E. et al., Laser-Based Analysis of Carbon Isotope Ratios. Science (1994) 263:945-947, retrieved from the Internet on Mar. 22, 2016 at <URL: http://science.sciencemag.org/content/263/5149/945.full-text.pdf+html>.
Mutschall, D. et al., Sputtered molybdenum oxide thin films for NH3 detection 1996 Sensor and Actuators B35-36, p. 320-324.
*Nanomedicon, LLC v. Research Found. of State Univ. of N.Y.*, 2012 NY Slip Op 33742(U), Mar. 15, 2012, Supreme Court, Suffolk County, Docket No. 36815-2010, Judge: Emily Pines, 14 pages.
O'Morain, Colm, Role of Helicobacter pylon in functional dyspepsia. World J Gastroentero. (2006) 12:2677-2680.
Otsuka America Inc., BreathTek Urea Breath Test, retrieved from the Internet on Mar. 31, 2016 at < http://web.archive.org/web/20120228152952/http://www.otsuka-us.com/Products/Pages/BreathTek.aspx>, 2 pages.
Papatheodoridis, George V. et al., Effects of Helicobacter pylori and nonsteroidal anti-inflammatory drugs on peptic ulcer disease: a systematic review. Clin Gastroenterol Hepato. (2006) 4:130-142.
Pardo, Matteo et al., Electronic Olfactory Systems Based on Metal Oxide Semiconductor Sensor Arrays. MRS Bulletin, Oct. 2004, pp. 703-708, Materials Research Society http://www.mrs.org/publications/.
Penner, J. L. et al., Serotyping of Campylobacter jejuni and Campylobacter coli on the Basis of Thermostable Antigens. Eur J Clin Microbial. (1983) 2:378-383.
Phillips, Michael, Detection of volatile organic compounds in breath. In "Disease markers in exhaled breath" eds Marczin N. Kharitonov SA, Yacoub MH and Barnes PJ. Marcel Decker. (2002) pp. 219-231, New York.
Prasad, A. K. et al., Comparison of sol-gel and ion beam deposited MoO3 thin film gas sensors for selective ammonia detection. Sens Actuators B. (2003) 93:25-30.
Prasad, A.K., et al., Reactivity sputtered Mo03 films for ammonia sensing. Thin Solid Films (2003) 436:46-51.
Quest Diagnositics, Helicobacter pylori Urea Breath Test (UBiT), retrieved from the Internet on Mar. 20, 2016 at <URL: http://www.questdiagnostics.com/hcp/topics/gastroent/hpylori_breath.html> 3 pages.
Romagnuolo, Joseph et al., Using Breath Tests Wisely in a Gastroenterology Practice: An Evidence-Based Review. Am J Gastroentero. (2002) 97: 1113-1126.
Ryan, M. A. et al., Polymer-Carbon Black Composite Sensors in an Electronic Nose for Air-Quality Monitoring; MRS Bulletin, Oct. 2004, pp. 714-719. Materials Research Society http://www.mrs.org/publications/.
Sberveglieri, G. et al., WO3 sputtered thin films for NOx monitoring, Sensors and Actuators B 26 (1995) pp. 89-92.
Slomianski, Arie et al., [13C]urea breath test to confirm eradication of Helicobacter pylori. Am J Gastroentero. (1995) 90:224-226.
Sonnenberg, Amnon et al., The Prevalence of Self-Reported Peptic Ulcer in the United States. Am J Public Health (1996) 86:200-205.
Stejskal, J., Polyaniline. Preparation of a Conducting Polymer (IUPAC Technical Report). Pure Appl. Chem., (2002) vol. 74, No. 5, pp. 857-867, International Union of Pure and Applied Chemistry.
Surveyor, Ivor et al., The 14C-urea breath-test for the detection of gastric Campylobacter pylori infection. Med J Aust (1989) 151:435-439.
Suslick, Kenneth S., An Optoelectronic Nose: "Seeing" Smells by Means of Colorimetric Sensor Arrays; MRS Bulletin, Oct. 2004, pp. 720-725, Materials Research Society http://www.mrs.org/publications/.
Timmer, Bjorn et al., Ammonia sensors and their applications—a review. Sensors and Actuators B, 2005, 107:666-677.
Vaira, Dino et al., Peptic ulcer and Helicobacter pylori: update on testing and treatment. Postgrad Med (2005) 117:17-22, 46. Retrieved from the Internet on Mar. 22, 2016 at <URL: http://dx.doi.org/10.3810/pgm.2005.06.1654> Taylor & Francis Ltd.
Versalovic, James, Helicobacter pylori. Pathology and diagnostic strategies. Am J Clin Patho (2003) 119:403-412. Retrieved from the Internet on Mar. 22, 2016 at <URL: http://ajcp.oxfordjournals.org>.
Wang, Xiaodong et al., An integrated array of multiple thin-film metal oxide sensors for quantification of individual components in organic vapor mixtures, Sensors and Actuators B, (1993) 13-14, 458-461.
Weir, Susan et al., Recurrent Bacteremia Caused by a "Flexispira"-Like Organism in a Patient with X-Linked (Bruton's) Agammaglobulinemia. J Clin Microbio (1999) 37:2439-2445. Retrieved from the Internet on Mar. 28, 2016 at <URL: http://jcm.asm.org>.
Winquist, F. et al., Electronic Tongues. MRS Bulletin, Oct. 2004, pp. 726-731, Materials Research Society http://www.mrs.org/publications/.
Xu, C. N. et al., Selective detection of NH over NO in combustion exhausts by using Au and MoO3 doubly promoted WO element. Sensors and Actuators B, (2000) 65, pp. 163-165.

\* cited by examiner

DIAGNOSTIC METHOD AND BREATH TESTING DEVICE

CROSS-REFERENCE TO RELATED APPLICATIONS

This application claims priority on U.S. Provisional Application 61/452,507 filed Mar. 14, 2011 which is incorporated herein by reference. This application also incorporates by reference U.S. Ser. No. 61/379,963 filed Sep. 3, 2010, U.S. Ser. No. 13/226,082 filed Sep. 6, 2011, and U.S. Ser. No. 61/452,391 filed Mar. 14, 2011.

TECHNICAL FIELD

The present invention relates to a diagnostic method and breath-testing device for the diagnosis of celiac disease or other gastrointestinal malabsorption in adults and children.

BACKGROUND OF THE INVENTION

The present application contains references to other publications. These publications are incorporated herein by reference.

Celiac disease is defined as a disease of the small bowel caused by a permanent intolerance to gluten. Most common symptoms of the disease are weight loss due to malabsorption, diarrhea, anemia, and growth failure. Celiac disease affects people of all ages and gender. Its incidence is on the rise worldwide due to environmental and genetic factors, currently affecting, on average, 1/300 people (children and adults) in the United States and in other developed nations. Up until recently celiac disease was considered a disease affecting predominantly people of Northern European origin this, however, is changing as cases are now reported in Asia and the Middle East, albeit at a much lower rate.

Definitive diagnosis of the disease is made on the basis of small bowel biopsies obtained while the patient is on gluten containing diet and after the patient is taken off gluten and free of symptoms. While small bowel biopsy is an invasive diagnostic modality there are other diagnostic methods currently available.

Currently available blood serum tests (Table 1) take place in centralized laboratories and measure antibodies to antigens produced in the patient's body due to gluten intolerance. Results are usually available in several days to a few weeks.

TABLE 1

Diagnostic blood tests for the diagnosis of celiac disease

| Test | Technology | Sensitivity | Specificity |
| --- | --- | --- | --- |
| Anti-tTG antibody | ELISA | 99% | >90% |
| IgA anti-endomysial antibody | Direct Immunofluerescence | 90% | 99% |
| Anti-gliadin antibody | ELISA Direct Immunofluerescence | Less sensitive | Less sensitive |
| Anti-deamidated gliadin antibody | Experimental | | |
| HLA-DQ2 | HLA typing | 94% | 73% |
| HLA-DQ8 | HLA typing | 12% | 81% |

In addition to blood testing for the presence of specific antibodies, as described in Table 1, blood serum can be tested for the presence of D-xylose, a sugar detected in serum one hour after the ingestion of carbohydrates. The D-xylose test is performed less frequently due to low sensitivity and specificity for the diagnosis of celiac disease and due to the broad use of the more specific antibody diagnostic tests.

Breath testing for the diagnosis of celiac disease has been investigated but is not currently used as a standard diagnostic method due to lower sensitivity (88%) and specificity (84%) when compared to the serum antibodies (Table 1). Tveito K. et al. (1) claim that 13C-xylose and 14C-xylose breath tests are diagnostic of celiac disease patients and both tests demonstrate high sensitivity (88%) and specificity (84%). These investigators also claim that the 13C-sorbitol breath test (2) for the diagnosis of celiac disease is superior to $H_2$-sorbitol test due to higher sensitivity and specificity, however well below the specificity/sensitivity of 13C-xylose breath test. All of these breath tests require the patient to ingest a carbohydrate substrate, either xylose or sorbitol and undergo breath testing every 30 minutes starting one hour post ingestion up to four hours post ingestion of the substrate. Hryniuk A et al. (3) who investigated the presence of volatile alcohols in the breath of patients with celiac disease report that no differences were found in the breath levels of methanol, propanol, butanol, heptanol or hexanol investigated using chemical ionization of breath air with $H_3O+$ and/or $NO+$ precursor ions in patients with celiac disease when compared to health subjects. All of the above described breath tests are based on spectroscopic analysis of the human breath content and take place at centralized laboratories. Rana, S V et al. (4) report that, at baseline, patients with celiac disease have significantly higher hydrogen in their breath than patients with functional bowel disease and normal subjects. Hydrogen breath test is a standard diagnostic modality for the diagnosis of lactose intolerance and other carbohydrate malabsorption but not for the diagnosis of celiac disease. The existing methodology for the detection of hydrogen in human breath in patients with lactose intolerance and bacterial overgrowth is through gas chromatography (Quintron Instrument Company).

SUMMARY OF THE INVENTION

The present invention consists of a novel, inexpensive, non-invasive, point-of-care, hand-held, device for the diagnosis of celiac disease using a selective hydrogen gas nanosensor.

Based on the present invention, a person, adult or child, suspected of having celiac disease or other type of gastrointestinal malabsorption, will provide one fasting breath sample through the mouth piece of the device. No ingestion of carbohydrate substrate is required. Data obtained in reducing the invention to practice proved that only celiac disease can be diagnosed with a fasting breath sample. This data shows that a test subject having a fasting breath sample in the range of 15-40 ppm hydrogen has celiac disease, not a different gastrointestinal disorder. No other gastrointestinal disorder will result in a fasting breath sample value in the 15-40 ppm hydrogen range.

DETAILED DESCRIPTION OF A PREFERRED EMBODIMENT

A preferred embodiment will be described, but the invention will not be limited to this embodiment.

The breath analyzer detects the presence of hydrogen in a human breath sample.

Figure 1:
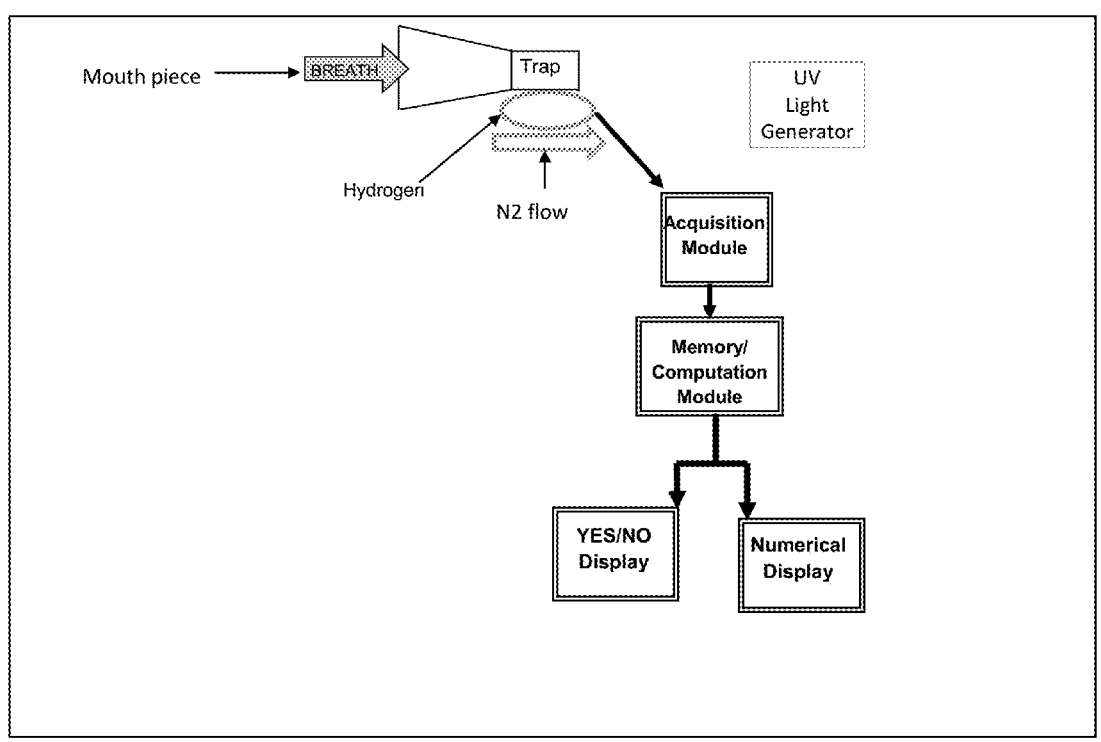
FIG. 1 is a schematic block diagram of a breath analyzer device for the detection of hydrogen in breath according to the invention.

FIG. 1 shows a sensor device which consists of a mouth piece, a trap for $CO_2$, $NH_3$ and $H_2O$, a hydrogen nanosensor, constant dry air flow and electronics. The electronics include an acquisition module, a memory/computation module, and two displays. The numerical display provides the concentration.

The YES/NO display will provide the person with an answer indicating high (above the established for this device threshold) or low (below the established for this device threshold) level of hydrogen in breath. A high level will indicate celiac disease or another type of gastrointestinal malabsorption, and a low level will indicate normal gastrointestinal absorption i.e. less likely celiac disease.

The sensor may be a nanosensor, or may be a hydrogen-selective film available from Giner, Inc., Newton, Mass., which it calls a trace gas sensor. (See, www.ginerinc.com)

The characteristics of the sensor according to the invention are that 1) it is hydrogen selective; 2) can be ZnO nanowire-based (100 n in diameter) or other type of hydrogen-selective film or nanosensor; 3) can be a single ZnO nanowire sensor fabricated using focused ion beam (FIB/SEM) instrument (5); and 4) can be capable of operating at room temperature requiring a small pulse UV light to recover.

Figures 2A, 2B:
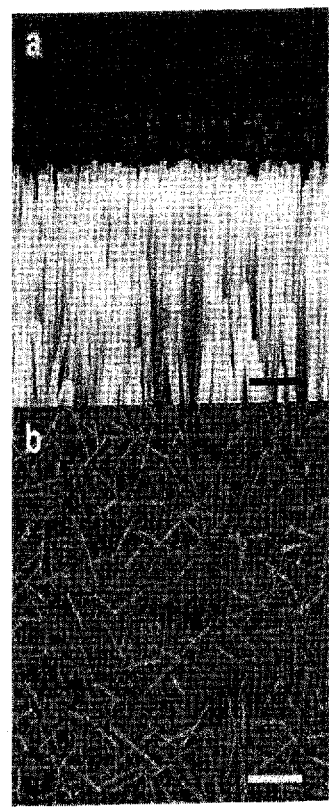
FIG. 2a is a scanning electron micrograph in cross-section of ZnO nanowires grown in deposition region at the entrance zone (ratio O/Zn>1)
FIG. 2b is a top view scanning micrograph of ZnO nanowires grown at the exit zone (ratio O/Zn<1)

FIG. 2a is a scanning electron micrograph in cross-section of ZnO nanowires grown in deposition region at the entrance zone (ratio O/Zn>1). Lupan O. et. al. (5)

FIG. 2b is a top view scanning micrograph of ZnO nanowires grown at the exit zone (ratio O/Zn<1). Lupan O. et. al. (5)

Figure 3:
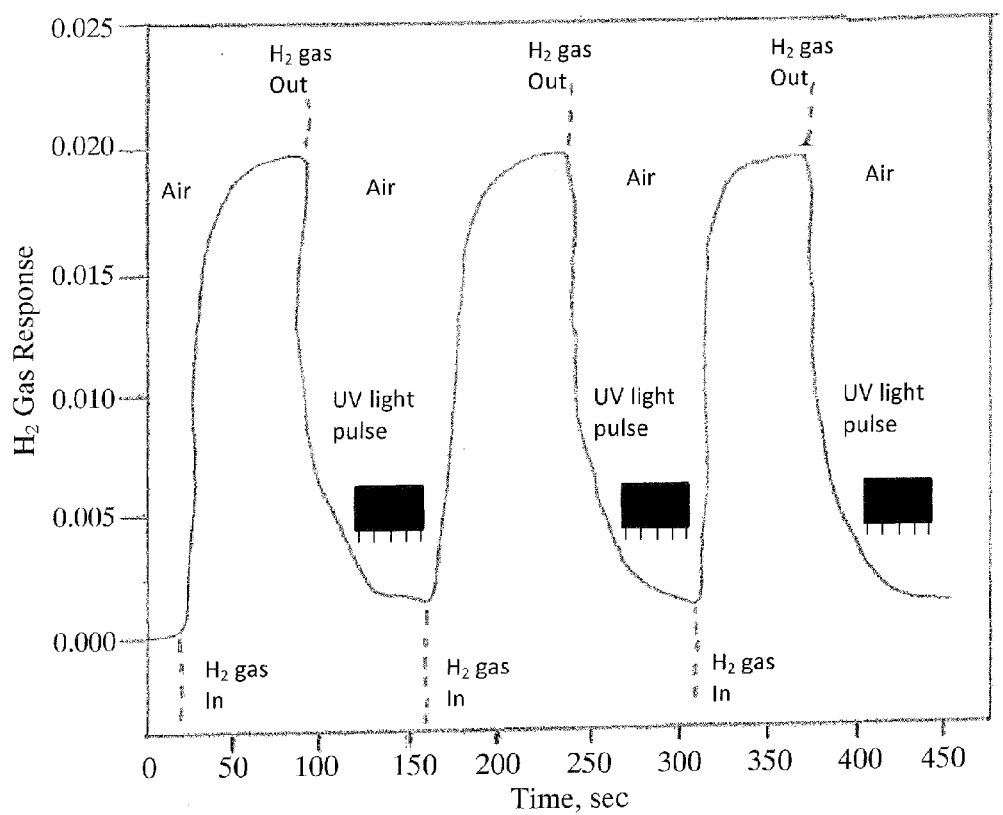
FIG. 3 is a graph showing the $H_2$ gas response for a 100 nm diameter $Z_nO$ NW-based sensor.

FIG. 3 is a graph showing the $H_2$ gas response for a 100 nm diameter $Z_nO$ NW-based sensor. The response curves of the individual nanowire-based sensor toward 10 ppm $H_2$ pulses. Before the test the nanowire was preconditioned in a constant dry air flow. An UV pulse is applied after $H_2$ is turned off. Lupan O. et al. (5).

Figure 4:
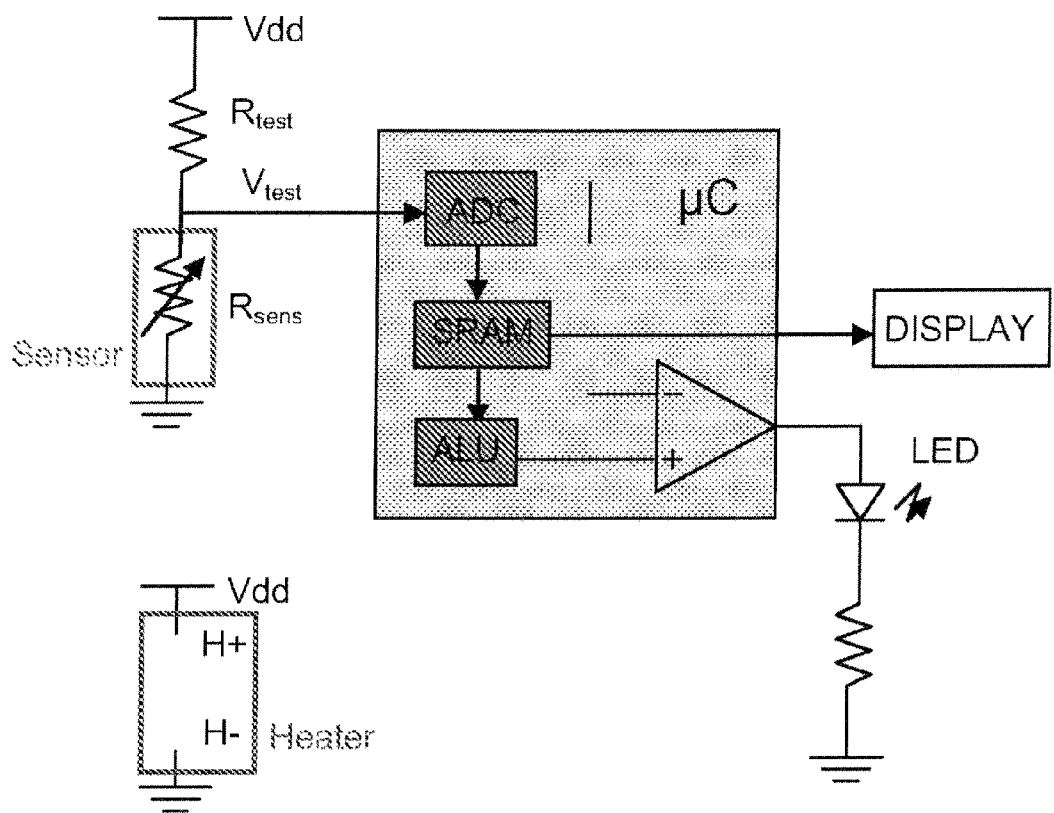
FIG. 4 shows electronic circuitry of a device according to the invention.

FIG. 4 shows the electronic circuitry of the device. FIG. 4 shows a sensor, interface circuitry and display. A microcontroller (μC) contains the Analog-to-Digital Converter memory (SRAM), and an Arithmetic Logic Unit (ALU). The V test is a voltage proportional to the resistance of the sensor. The sensor will detect hydrogen gas. If one wishes to detect gases other than hydrogen, other sensors could be used. More than one sensor could be incorporated, with a switch to select connection of the sensor to the circuit for the specific gas to be detected.

Although one preferred embodiment has been shown and described, the invention is not limited to this embodiment, and the scope is defined by reference to the following claims.

REFERENCES 1. 13C-xylose and 14C-xylose breath test for the diagnosis of coeliac disease. *Scandinavian J Gastroenterol* 2008; 43(2): 166-73; Tveito K. et al
2. A novel one-hour 13C-sorbitol breath test versus the H2-sorbitol breath test for assessment of coeliac disease. *Scand J. Gastroenterol.* 2009; 44(7):813-9; Tveito K. et al
3. A preliminary investigation of exhaled breath from patients with celiac disease using selected ion flow tube mass spectrometry. *J Gastrointestin Liver Dis.* 2010 March; 19(1):15-20; Hryniuk A, Ross B M
4. Influence of previously ingested wheat on fasting breath hydrogen in celiac patients. *Dig Dis Sci.* 2009 June; 54(6):1276-9. Rana S V et al.
5. Selective hydrogen gas nanosensor using individual ZnO nanowire with fast response at room temperature. *Sensors and Actuators B* 144 (2010) 56-66; Lupan O. et al

What is claimed is:

1. A method of diagnosing celiac disease in a subject comprising:
   providing a hand-held breath detector comprising a mouthpiece, a trap and a hydrogen selective sensor which operates at room temperature and detects a hydrogen concentration at levels as low as 10 ppm in a breath sample;
   using the hand-held breath detector on a subject to detect a hydrogen concentration in a fasting breath sample of the subject, wherein the fasting breath sample of the subject is taken without requiring the subject to ingest a xylose or sorbitol carbohydrate substrate within one hour to four hours of the breath test; and
   diagnosing celiac disease in the subject if the hydrogen concentration in the fasting breath sample is above a threshold concentration.

2. The method according to claim 1, wherein the sensor is a nanosensor.

3. The method according to claim 1, wherein the sensor is a film sensor.

4. The method according to claim 3, wherein the sensor is a thin film sensor.

5. The method according to claim 1, further comprising acquiring an output signal from the hydrogen selective sensor which has a characteristic indicating a detected hydrogen concentration, using a computation module to compute the detected hydrogen concentration, and displaying the results of the computation.

6. The method according to claim 1, comprising displaying a numerical result indicating a detected hydrogen concentration.

7. The method of claim 1, comprising comparing a detected hydrogen concentration to a threshold amount, and displaying whether the amount has been exceeded, or is less than the threshold.

8. The method of claim 1, comprising using a hydrogen selective sensor comprising a ZnO nanowire-based sensor.

9. The method of claim 1, further comprising using a UV light pulse to recover the detector for repeated uses.

* * * * *